(12) United States Patent
Popp et al.

(10) Patent No.: US 7,715,002 B2
(45) Date of Patent: May 11, 2010

(54) METHOD FOR CLASSIFYING SCIENTIFIC MATERIALS SUCH AS SILICATE MATERIALS, POLYMER MATERIALS AND/OR NANOMATERIALS

(75) Inventors: Michael A. Popp, Neumarkt (DE); Guenther Bonn, Zirl (AT); Christian W. Huck, Innsbruck (AT)

(73) Assignee: Bionorica AG, Neumarkt (DE)

( * ) Notice: Subject to any disclaimer, the term of this patent is extended or adjusted under 35 U.S.C. 154(b) by 357 days.

(21) Appl. No.: 11/626,321

(22) Filed: Jan. 23, 2007

(65) Prior Publication Data

US 2008/0177481 A1 Jul. 24, 2008

(51) Int. Cl.
*G01J 3/42* (2006.01)
*G01N 21/35* (2006.01)

(52) U.S. Cl. .................. 356/300; 356/51; 250/341.8

(58) Field of Classification Search ............... 356/319, 356/323, 325
See application file for complete search history.

(56) References Cited

U.S. PATENT DOCUMENTS 4,291,975 A * 9/1981 Raccah .................. 356/30

| | | |
|---|---|---|
| 7,244,902 B2 | 7/2007 | Popp et al. |
| 2004/0222136 A1 | 11/2004 | Popp et al. |

FOREIGN PATENT DOCUMENTS

| DE | 19538932 A1 | 4/1997 |
|---|---|---|
| DE | 19945392 A1 | 3/2001 |
| DE | 10124917 A1 | 12/2002 |
| DE | 102004009306 A1 | 9/2005 |

OTHER PUBLICATIONS

Christian W. Huck, Robert Ohmacht, Zoltan Szabob and Günther K. Bonn, Near infrared spectroscopy, cluster and multivariate analysis—characterisation of silica materials for liquid chromatography, Journal of Near Infrared Spectroscopy, 2006, vol. 14, p. 51-57.

* cited by examiner

*Primary Examiner*—F. L Evans
(74) *Attorney, Agent, or Firm*—Patent Central LLC; Stephan A. Pendorf (57) ABSTRACT

A method is provided for characterizing a scientific material, such as a silicate material, a polymer material and/or nanomaterial. The method can include the steps of irradiating a measuring light of a predetermined wavelength range into material specimens, recording the measuring light reflected and/or reemitted by the material specimens, determining a ratio depending on the wave lengths of irradiated to detected measuring light (spectrum), and numerical-mathematical processing of spectral data of single material specimens for determining the characteristic features of the material specimens.

23 Claims, 5 Drawing Sheets

METHOD FOR CLASSIFYING SCIENTIFIC MATERIALS SUCH AS SILICATE MATERIALS, POLYMER MATERIALS AND/OR NANOMATERIALS

FIELD OF THE INVENTION

The present invention relates to a method for characterizing and classifying scientific materials.

SUMMARY OF THE INVENTION

In particular the present invention relates to a method of characterizing scientific materials such as silicate materials, polymer materials and/or nanomaterials of different origins and to a method for classifying scientific materials, such as silicate materials, polymer materials and/or nanomaterials of different origins.

BACKGROUND OF THE INVENTION

In industry, silica gel is traditionally used as adsorbent. It is used to adsorb vapors, e.g., from petrol, benzene, ether, alcohol, from air, e.g., in the celluloid-, silk-, lacquer- and explosives-factories. Silica gel is a good desiccant; it can be used for gases, liquids and even solids can be dried (e.g. in a desiccator), liquids and lipids can be purified and decolorized. Silica gel can be used as a support medium for catalysts, as deodorant, and as drying material, as well as an active ingredient in filtertips for cigarettes. It is also used to coat electrodes in electrochemical cells or accumulators. Other fields of application comprise lacquer, synthetic materials, adhesives, toothpaste, etc.

In chemistry, silica gel is used, e.g., in chromatography as a stationary phase. In column chromatography the stationary phase is most often composed of silica gel particles of 1.5-60 μm. In this application, due to silica gel's polarity, non-polar components tend to elute before more polar ones. Lipophilic groups may be attached to the silica gel surface to produce a reverse phase silica gel which elutes polar components first. Silica gel is also applied to aluminum or plastic sheets for thin layer chromatography. For high-performance liquid chromatography (HPLC) in the fields of proteomics, metabolomics and phytomics silicate materials are also frequently used. In order to achieve the highest separation efficiencies, the physical properties of silica particles such as particle size, pore volume and surface area play an essential role.

The size of the particles is usually determined by electron microscopy, light scattering or the Coulter-Counter method, the surface area is measured by nitrogen adsorption experiments according to the Brunnauer Emmet Teller (BET) theory, pore sizes and volumes are usually assessed by size exclusion chromatography (SEC).

Nanotechnology is a field of applied science focused on the design, synthesis, characterization and application of materials on the nanoscale, so called nanomaterials. Nowadays nanomaterials play important roles in colloidal science, biology, physics, chemistry and other scientific fields that involve the study of phenomena and manipulation of material at the nanoscale and serve essentially to extend existing sciences into the nanoscale.

Two main approaches exist to produce nanomaterials: one is a "bottom-up" approach where materials are built up atom by atom, the other a "top-down" approach where they are synthesized or constructed by removing existing material from larger entities.

A unique aspect of nanomaterials is the vastly increased ratio of surface area to volume, which opens new possibilities in surface-based science, such as catalysis. This catalytic activity also opens potential risks in their interaction with biomaterials.

The impetus for nanotechnology has stemmed from a renewed interest in colloidal science, coupled with a new generation of analytical tools such as the atomic force microscope (AFM) and the scanning tunneling microscope (STM). Combined with refined processes such as electron beam lithography, these instruments allow the deliberate manipulation of nanostructures.

General fields involved with proper characterization of nanomaterials include physics, chemistry, and biology, as well as mechanical and electrical engineering.

However, due to the inter- and multidisciplinary nature of nanotechnology, subdisciplines such as physical chemistry, materials science, or biomedical engineering are considered significant or essential components of nanotechnology.

The proper characterization of nanomaterials is a dominant concern of nanotechnologists. The atomic force microscope (AFM) and the Scanning Tunneling Microscope (STM) are two early versions of scanning probes that launched nanotechnology. There are other types of scanning probe microscopy, all based on the idea of the STM, that make it possible to see structures at the nanoscale. This is why scanning probe microscopy has become an important technique for the characterization of nanomaterials. However, all these tools are difficult to handle, require a lot of skill and expertise along with a tedious preparation and furthermore are slow and expensive.

Polymer is a term used to describe molecules consisting of structural units and a large number of repeating units connected by covalent chemical bonds. The key feature that distinguishes polymers from other molecules is the repetition of many identical, similar, or complementary molecular subunits in these chains. These subunits, the monomers, are small molecules of low to moderate molecular weight, and are linked to each other during a chemical reaction called polymerization. Instead of being identical, similar monomers can have various chemical substituents. The differences between monomers can affect properties such as solubility, flexibility, and strength.

Although most polymers are organic, with carbon-based monomers, there are also inorganic polymers; for example, the silicones, with a backbone of alternating silicon and oxygen atoms and polyphosphazenes.

Physical properties of polymers include the degree of polymerization, the molar mass distribution, crystallinity, as well as the thermal phase transitions, branching and stereoregularity or tacticity.

Interestingly, polymer substrates are used for everyday banknotes in Australia, Romania, Papua New Guinea, Samoa, Zambia, Vietnam, New Zealand and a few others, and the material is also used in commemorative notes in some other countries.

The characterization of a polymer requires several parameters which need to be specified. This is because a polymer actually consists of a statistical distribution of chains of varying lengths, and each chain consists of monomer residues which affect its properties. A variety of lab techniques are usually used to determine the properties of polymers. Techniques such as wide angle X-ray scattering, small angle X-ray scattering, and small angle neutron scattering are used to determine the crystalline structure of polymers. Gel permeation chromatography is used to determine the number average molecular weight, weight average molecular weight, and polydispersity. FTIR, Raman and NMR can be used to determine composition.

However, similarly as for silicate materials and nanomaterials these methods require a complex and expensive instrumentation and a good deal of expertise, time and effort.

Nevertheless, in all these applications, the physicochemical characterization of these scientific materials is of great importance. Only well characterized and optimized materials can be used in demanding fields.

Furthermore, in demanding fields it is oftentimes important to make sure that the scientific materials that are used are continuously from the same source to ensure an excellent reproducibility.

SUMMARY

In this respect it was the object of the present invention to provide a fast, efficient and easy-to-use method to characterize and/or to classify scientific materials such as silicate materials, polymer materials and/or nanomaterials.

It has been found that near infrared reflectance spectroscopy (NIRS) offers the benefits of improved sample handling, reduced costs and the possibility to measure chemical and physical properties supported by sophisticated statistical software to perform principal component analysis (PCA) or regression (PCR) or partial least square regression (PLSR).

In the past, most NIRS dealt with the analysis of protein and moisture content in many foods and pharmaceutical products.

The present inventors have now surprisingly found that they could use NIRS as a fast, precise, reliable, user friendly, non destructive and robust technique for the characterization and/or classification of scientific materials such as silicate materials, polymer materials and/or nanomaterials.

In particular the present invention provides a method for characterizing scientific material such as a silicate material, a polymer material and/or nanomaterial comprising the following steps:
  a) irridating a measuring light of a predetermined wavelength range into the material specimens;
  b) recording the measuring light reflected and/or reemitted by the material specimens;
  c) determining a ratio depending on the wave lengths of irradiated to detected measuring light (spectrum); and
  d) numerical-mathematical processing of the spectral data of the single material specimens for determining the characteristic features of the material specimens.

If the scientific material is a silicate material then it is preferred that the silicate material is a silica gel, preferably a silica gel for chromatographic separation procedures. Since the nature of the silica gel in chromatographic separation procedures has a significant effect on the separation properties of the column material it is of great importance to gather information about the individual properties of the material. Companies that produce silica gel need to ensure that the material they produce has the exact same properties between charges, so that one important field of application of the method of the present invention is quality control.

If the scientific material is a polymer, it is preferred that the polymer is one that is to be used in demanding high tech applications that are sensitive to the material properties of the polymer. Typical examples are poly(styrene/divinylbenzene) (PS/DVB) or a poly(glycidylmethacrylate/divinylbenzene). As the method of the present invention is a very quick and sensitive method it further allows to observe the polymerization process, so that it can be optimized, i.e. that a polymer is achieved having the desired characteristics, such as particle size or porosity, for instance.

Generally the scientific material can be derivatized. Preferred derivatizations are those with $C_1$-$C_{20}$, in particular with $C_{18}$, $C_8$, $C_4$ or phenyl groups and/or with IMAC or with ion-exchange affinity conferring groups.

If the scientific material is a nanomaterial it is preferred that the nanomaterial is a derivatized nanomaterial. Derivatizations often have significant effects on the final material properties, so that by the application of the method of the present invention one can, e.g., check whether or not or to what extent a nanomaterial is derivatized and/or how it is derivatized. Particular examples of nanomaterials that optionally are derivatized are carbon nanotubes, fullerenes or nano fibers. In principle any kind of derivatization is feasible that does not render the nanomaterial useless for any purpose or that does not change the material in such a way that it can no longer be considered a nanomaterial.

In case the scientific material is derivatized with for instance $C_{18}$, $C_8$, $C_4$ or phenyl groups and/or with IMAC or with ion-exchange affinity conferring groups, an important feature of this scientific material for the use as a stationary phase in a separation method is the degree of surface coverage. With the analytical methods used so far the determination of the degree of surface coverage was time consuming and cost-intensive. However, with the method of the present invention it is possible to determine the degree of surface coverage in a fast, efficient and easy way.

The method of the present invention allows in principle to characterize any physical or chemical property of the scientific material in question, however, it is most often required and, hence preferred, to characterize features such as particle size, the specific surface area, the derivatization, the pore porosity, the pore size and/or the pore diameter. All this can easily be achieved with the method of the present invention.

To carry out the method of the present invention the sample is irradiated with radiation and the reflected and/or reemitted radiation is detected and analyzed. Consequently any radiation can be used that is at least either reflected by the sample or that causes the sample to reemit radiation and wherein the reflected and/or reemitted radiation can be detected by any means known to those skilled in the art.

Consequently the method of the present invention is not limited to any specific kind of radiation. However for reasons of safety and of ease to handle it is preferred that the predetermined wavelength range is in the NIR-VIS wavelength range, in particular in the range of approximately 400 to 2,500 nm (4,000-14,186 $cm^{-1}$), preferably in the range of approximately 1,000 to 2,200 nm (4,500 to 10,000 $cm^{-1}$).

The method of the present invention can be successfully carried out, if at least a part of the measuring radiation reaches the sample and at least a part of the reflected and/or reemitted radiation reaches the detector.

However the accuracy of this method can be improved and/or the noise can be minimized by avoiding or minimizing interactions of the measuring radiation and/or the reflected and/or reemitted radiation with matter that does not belong to the sample to be tested. One possibility to achieve this would be to analyze the sample in a vacuum. Another more preferred since easier to use embodiment of the present invention is that the measuring radiation, e.g., light, is conducted to the material specimens via a radiation conductor, e.g., light conductor, and/or is absorbed by the material specimens.

In a preferred embodiment of the present invention the optical thickness of the specimen layer can be in the range of approximately 0.2 to approximately 5 mm, preferably in the range of approximately 0.5 to approximately 3 mm. Specimens with a smaller optical thickness than 0.2 mm are usable as well as long as this is still enough material, that any effects can be measured. According to this, the NIRS method was tested to be also sensitive enough to detect even coatings with a film thickness of approximately 100-150 µm. Thicker materials are also applicable as long as still a measurable signal can be obtained. For instance, by measuring the sample of interest in diffusive reflection mode, a high thickness of the material will be no problem.

In order to ensure a good reproducibility and comparability of the measured data it is preferred that the material specimens are thermostated. While in principle any temperature is suitable where the sample to be analyzed is still in a state showing comparable and reproducible characteristics it is nevertheless preferred to use approximately 23° C., for the measurement. This saves energy and reduces the preparation time for the samples.

While the obtained spectra can in principle be analyzed as they are without any further numerical-mathematical processing it is more convenient to process the obtained raw data, e.g., in order to eliminate noise or to reduce file sizes.

It is preferred, however, that the numerical-mathematical processing comprises a data reduction, in particular by: normalization, smoothing, in particular according to Savitzky Golay, 1st derivation, 2nd derivation, multiplicative scatter correction, reciprocal value, square, mean centering, Kubelka Munc Transformation, absorption, baseline correction, addition of a constant, shift negative to zero, principal component analysis (PCA), principal component regression (PCR), partial least squares regression (PLS).

A further embodiment of the present invention is a method for characterizing a scientific material, such as a silicate material, a polymer material and/or nanomaterial comprising the following steps:

a) providing a plurality of material classes each with a plurality of calibration and material specimens per class with a plurality of known class-characteristics;

b) irradiating a measuring light of an predetermined wavelength range into the material specimen;

c) recording of the measuring light passed through, reflected, reemitted and/or scattered by the material specimens;

d) determining a ratio depending on the wave lengths of irradiated to detected measuring light (spectrum) for each material specimen of a class;

e) numerical-mathematical processing of the spectral data of the individual material specimens;

f) correlating the spectra of a majority of material specimens with a predetermined material class;

g) creating a database with the processed spectral data with different material classes based on the material specimens measured of the individual classes for calibration of a class correlation;

h) repeating steps b) to e) at least once with at least one material sample with at least partially unknown characteristics; and i) determining the material classes to which the unknown material specimen is related, by means of a class correlation of the spectra measured using the created calibration database from step g).

By the method of the invention it is possible for the first time to classify a scientific material, e.g., with regard to its producer.

The scientific material is preferably a silicate material, a polymer or a nanomaterial.

Similar as in the method for characterizing a scientific material also for this method the silicate material can be a silica gel, preferably a silica gel for chromatographic separation procedures and/or the polymer can be for instance a poly(styrene/divinylbenzene) (PS/DVB) or a poly(glycidylmethacrylate/divinylbenzene) and/or the nanomaterial can be a derivatised nanomaterial, in particular a carbon nanotube, fullerene or a nano fiber wherein the derivatization is preferably with $C_{18}$, $C_8$, $C_4$, phenyl, IMAC or with ion-exchange affinity conferring groups.

Those skilled in the art will understand, that the features described for the method for characterizing a scientific material also apply to the method for classifying a scientific material.

In particular this is the case for the preferred wavelength range of the radiation used, for the preferred way the radiation is guided to and received from the sample and to the preferred dimensions of the sample to be analyzed.

The expression "class" is understood, for the purposes of the present invention, as a group of scientific materials of the same nature, e.g., silicate material, polymer material or nanomaterial, having defined properties, i.e. class properties, such as, e.g., the particle size, the specific surface area, the derivatization, the pore porosity, the pore size and/or the pore diameter.

Thus, for instance, the material class "silica gel, Type x of manufacturer A" may exhibit the class properties: particle size: "0.05 mm +/−0.01 mm", specific surface area: "0.00125 $mm^2$ +/−0.00075 $mm^2$" and pore diameter: "0.005 mm +/−0.001 mm".

Hence, in a preferred embodiment of the present invention the method of the invention allows classification of samples class properties, at least partially selected from the following group: particle size, particle surface, pore diameter, pore volume, derivatization, pore porosity.

By the method of the invention it was possible by way of example to achieve an unambiguous classification with unknown silica gel samples for several manufacturers.

In accordance with the present invention it is preferred to record an NIR spectrum of the samples in question without any further preparation of samples. This saves time and unnecessary effort. For this method, e.g., a commercially available NIR-VIS spectrometer may be used. Numerical-mathematical conditioning of the spectral raw data may be carried out with an equally commercially available software, e.g., BCAP V 6.00 [BÜHLER AG, ANATEC, CH-9240 Uzwil, Switzerland].

Class correlation may also be performed with a commercially available software, such as Nircal 3.0 [Buchi AG, CH-9230 Flawil 1], e.g., through principal components analysis and clustering. The result may be represented, for example, in the form of a cluster representation as a 3-D plot, wherein the axes represent the principal components.

In order to calibrate the method of the invention, initially of a plurality of samples known with regard several class properties (as a rule at least 10 samples/class property) one respective NIR spectrum is measured, as a rule repeatedly, in order to buffer statistical variations. This data is as a rule conditioned numerically-mathematically in order to reduce the bulk of data and to concentrate on the essential characteristics of the spectra.

Then the method is correlated with these samples such that multivariate methods like principal components analysis, clustering, artificial neuronal networks, are applied to this conditioned data, to be able to state based on the abundant data whether or not an unknown sample, when also measured by NIR spectroscopy, belongs to this class.

Multivariate methods refer to evaluation methods utilizing more than just one measurement signal of a same sample in order to arrive at an analysis result. Among these methods there are i.a. Multi-linear Regression (MLR), Principal Components Analysis (PCA), Principal Components Regression (PCR), the method of Partial Least Squares (PLS), clustering methods, and artificial neuronal networks.

In clustering methods it is preferred if the tolerance areas of the individual clusters are adjustable during calibration.

For the artificial neuronal networks in particular the following algorithms may be considered: backpropagation networks, Dynamic Learning Vector Quantization (DLVQ algorithm), Radial Basis Functions (RBF networks), in particular RBF networks (RBF-DDA networks) trained with the Dynamic Decay Adjustment algorithm (DDA algorithm).

PCA performs a separation of the original data matrix into two matrices, referred to as factor values and loadings. In the original data space a vector is selected in such a way that a maximum possible part of the variance is imaged when projecting the data onto it. This vector is the first principal component. A second principal component is orthogonal to the first principal component, and optionally a third principal component is orthogonal to the first and second principal components, wherein the second and third principal components are to image as much as possible of the variance not described yet by the first and second principal components, respectively.

The coordinates along the first principal component contain the essential information of the data, with the second and third principal components essentially reflecting scattering.

This process is repeated until either the number of the principal components corresponds to that of the dimension of the starting data, or until a particular termination criterion is reached.

The principal components thus obtained are linear combinations of the original dimensions. They are linearly independent of each other, so that a defined number of principal components contains less redundant information than the same number of starting variables.

Moreover the thus-obtained principal components each describe a maximum possible variance of the starting data not described yet by the already existing principal components. As a result, generally the first three to five principal components reflect the essential proportion of the information in the set of data.

Mathematically speaking, principal components analysis is a characteristic value problem, the fundamental solution of which is known to the person having skill in the art.

The result of principal components analysis also is a transformation of the N-dimensional original data space, with the result that the first dimensions contain the essential data portions strongly contributing to the overall variance, and the last dimensions basically reflecting no more than the noise content. In this way the structure of the spectroscopic data in question may be represented by plotting the first principal components relative to each other. As a two-dimensional, preferably 3-D, image they are then available for visual evaluation to the user who is left with the option of selecting a representation that enables a classification of samples into particular classes and which may, of course, also be automated.

In calibration, the so-called tolerance circles of the images may then be selected so as to be adaptable to particular classes, where necessary, in order to facilitate classification.

Preferably about 70% of the totality of samples measured per class are used for calibration, and about 30% for validation of the method of the invention.

It is also preferred that approximately 3 to 20 spectral-scans/material specimen are recorded.

For a better reproducibility of the method of the invention, the samples are measured at a constant temperature, preferably at approximately 23° C.

It is obvious to those skilled in the art that it is possible to freely combine any features disclosed herein without departing from the scope of the invention as disclosed.

The applicant furthermore makes reference to the full disclosure of all references cited herein.

Further preferred embodiments of the present invention are set forth in the subclaims.

BRIEF DESCRIPTION OF DRAWINGS

Further advantages and features of the present invention result from the description of embodiments, of experimental examples and by reference to the drawings, wherein.

DETAILED DESCRIPTION OF EXPERIMENTAL EXAMPLES

Silica Materials

Prontosil 60 (3 µm, 60 Å, 450 $m^2 \times g^{-1}$), Prontosil 120 (3 µm, 120 Å, 300 $m^2 \times g^{-1}$), Prontosil 300 (3 µm, 300 Å, 100 $m^2 \times g^{-1}$), Prontosil with 120 Å and different particle diameters 3, 5, 10, 15, 20 µm and Prontosil with 5 µm particle diameter and 60, 120, 200 and 300 Å pore diameter were purchased from Bischoff (Leonberg, Germany), Nucleosil $C_8$ (5 µm, 300 Å, 100 $m^2 \times g^{-1}$), Nucleosil $C_{18}$ (5 µm 300 Å, 100 $m^2 \times g^{-1}$), Nucleosil 1000 $C_{18}$ (7 µm, 1000 Å, 25 $m^2 \times g^{-1}$) and Nucleosil 4000 $C_{18}$ (7 µm, 4000 Å, 10 $m^2 \times g^{-1}$) from Agilent (Waldbronn, Germany), Hypersil $C_{18}$ BDS (3.5 µm, 130 Å, 170 $m^2 \times g^{-1}$), Spherisorb $C_{18}$ (3, 5, 10 µm, 80 Å, 220 $m^2 \times g^{-1}$), Spherisorb $C_8$ (3, 5, 10 µm, 80 Å, 220 $m^2 \times g^{-1}$) were from Waters (Milford, USA).

For the determination of particle size non porous silica Micra (1.5 µm), which was purchased from Micra Scientific (Northbrook, Ill., USA), was included in the model. All other silica phases, Amino 4µ (4 µm, 126 Å, 317 $m^2 \times g^{-1}$), Amino A21 (10 µm, 114 Å, 317 $m^2 \times g^{-1}$), Amino A23 (6 µm, 117 Å, 310 $m^2 \times g^{-1}$), Silica 622 (14 µm, 91 Å, 431 $m^2 \times g^{-1}$), Silica 191-1 (6 μm, 74 Å, 458 m²×g⁻¹), Silica 191-2 (6 μm, 74 Å, 458 m²×g⁻¹), Silica 191-3 (6 μm, 74 Å, 458 m²×g⁻¹), ODS 2 (6 μm, 74 Å, 308 m²×g⁻¹, non endcapped), ODS 3 (6 μm, 78 Å, 267 m²×g⁻¹, endcapped) were homemade.

NIR-Spectroscopy

NIR spectra were recorded with a scanning polarization interferometer NIR-spectrometer (Büchi, Uzwil, Switzerland) crosswise over a wavelength range from 4500 to 10000 cm⁻¹ using an optic glass fiber (silica glass, lnfrasil, Bes Optics Inc., Warwick, Great Britain, length 2 m) in reflectance mode. There was no distance between the top of the fiber and the sample; measurements were carried out applying slight pressure onto the sample.

Ten scans were used for one average spectrum to equilibrate in homogeneities. Chemometrical software NirCal 3.0 and 4.0 (Büchi) was used for creating a model. Samples were thermostated in a water bath to 23° C. (model PCM, Julabo, Seelbach, Germany), randomly divided into a so called learning-set (75%), and a test set (25%).

The optimum number of factors used for the individual prediction was determined by cross-validation. Quality of cluster analysis was described in the Q-value calculated by the NirCal 7 4.0 software. The selection of the best quantitative regression model is generally—not only in these specific examples—based on the following calculated values:

1) BIAS, i.e., the average deviation between the predicted values ($y_n$) and the actual values ($x_n$), in the calibration-set, should be close to zero.

$$\text{Bias} = \frac{1}{N}\sum (x_n - y_n)$$

2) PRESS, Predicted Residual Error Sum Square is the sum of the square of the deviation between predicted and reference values. The PRESS value of the validation set should be as small as possible and similar to that of the calibration set.

$$\text{PRESS} = \Sigma(x_n - y_n)^2$$

3) Standard error of estimation (SEE), i.e., the standard deviation of the differences between reference values and NIRS-results in the calibration set.

$$SEE = \sqrt{\frac{1}{N}\Sigma(x_n - y_n - \text{Bias})^2}$$

4) Standard error of prediction (SEP), i.e., the counterpart for the test-set samples. SEE and SEP should be as small as possible.

$$SEP = \sqrt{\frac{1}{N}\Sigma(x_n - y_n - \text{Bias})^2}$$

5) The correlation coefficient ($R^2$) should approach 1.

Preparation of the Homemade Starting Silicas

Starting silica has been sized in the Applicant's laboratory with an average particle size, pore diameter, specific surface area and pore volume provided above. Further preparation of the phases was carried out as described earlier (Szabo et al., J. Sep. Sci. 28, 313, 2005; Halasz, et al., Angewandte Chemie 90, 954 (1978); Halasz et al., Berichte der Bunsengesellschaft 79, 731 (1975); Ohmacht, Magy Kern F. 89, 229 (1983); Werner, et al., Chromatogr. Sci. 18, 277 (1980); Crispin, et al., Chromatogr. 239, 351 (1981)).

Reference Measurements

Particle size, pore diameter, specific surface area, total porosity, pore porosity and pore volume were determined and calculated following the size-exclusion chromatographic methods previously published (Halasz, et al., Angewandte Chemie 90, 954 (1978); Halasz et al., Berichte der Bunsengesellschaft 79, 731 (1975); Ohmacht, Magy Kern F. 89, 229 (1983); Werner, et al., Chromatogr. Sci. 18, 277 (1980); Crispin, et al., Chromatogr. 239, 351 (1981)). In the case of commercially available materials the information provided by the producer was used.

Identification of Silica Particles with Different Surface Morphology and/or Derivatization The Applicant generated a qualitative model based on principal component regression (PCR), which allows clustering silica particles with differences in particle size and/or surface area, pore structure, derivatization, in a 3 dimensional factor plot. Differences in pore structure can be visualized by scanning electron microscopy.

Figure 1:
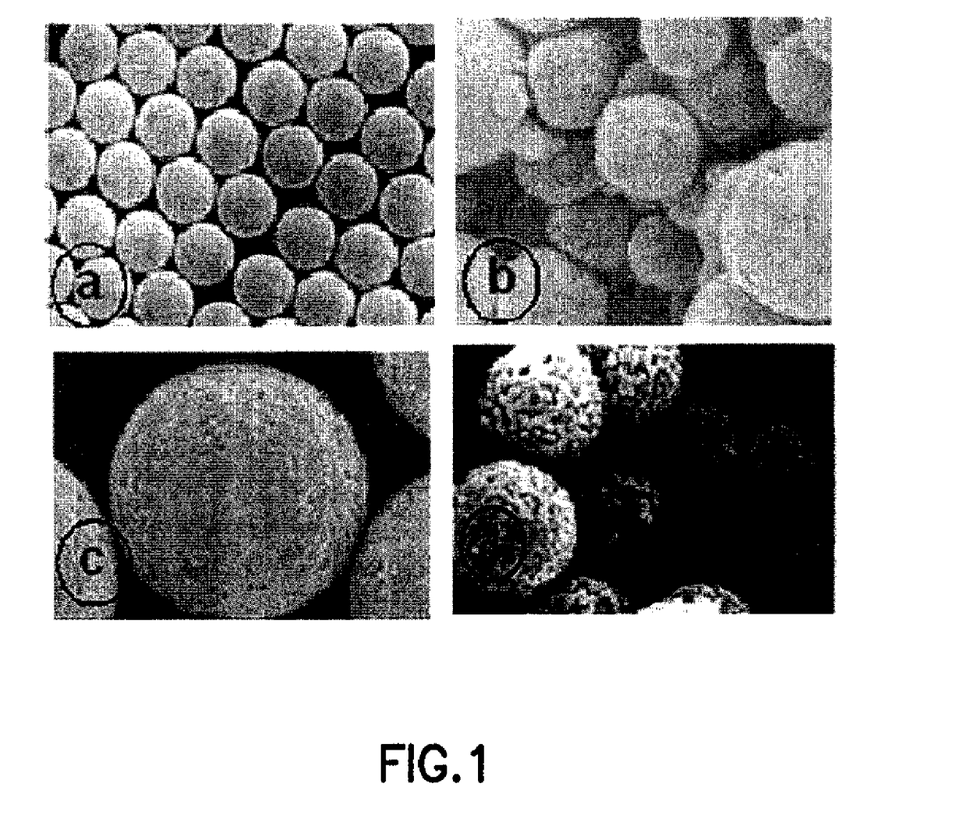
FIG. 1 is an electron micrograph of silica particles with different porosities: a: non-porous (2000×); b: 60 Å (5000×); c: 300 Å (6000×); d: 1000 Å (4000×)
Figure 2:
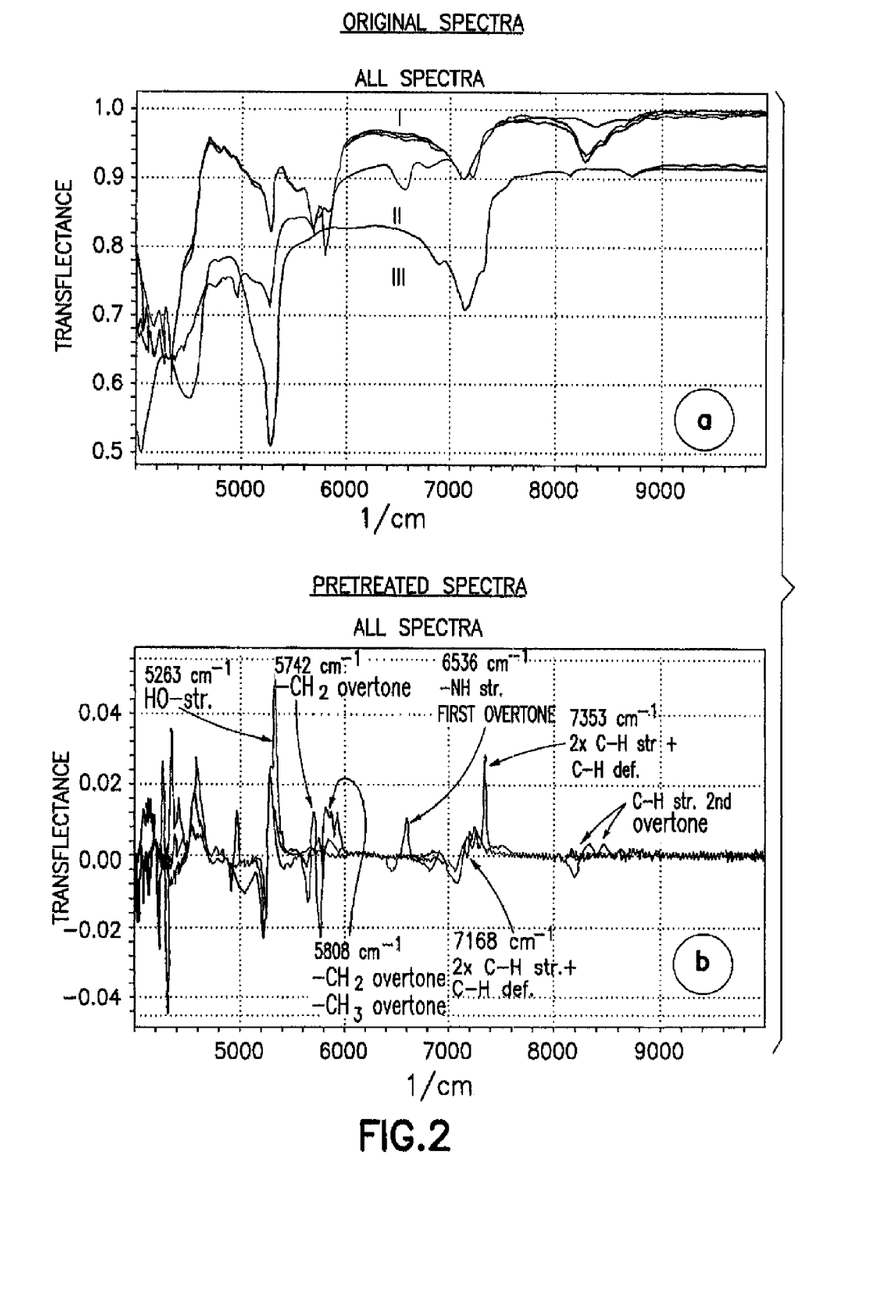
FIG. 2 are NIRS-spectra of silica particles with different porosity and derivatization (10 measurements), a: original spectra; b: pretreated spectra with marked characteristic vibrations (calculation of its $1^{st}$ derivative Taylor 3 points); wave number range: 4500-9996 $cm^{-1}$; reflectance; scans: 10; temperature: 23° C.; sample I: octadecylated silica; sample II: amino derivatized silica; sample III: pure silica.
Figure 3:
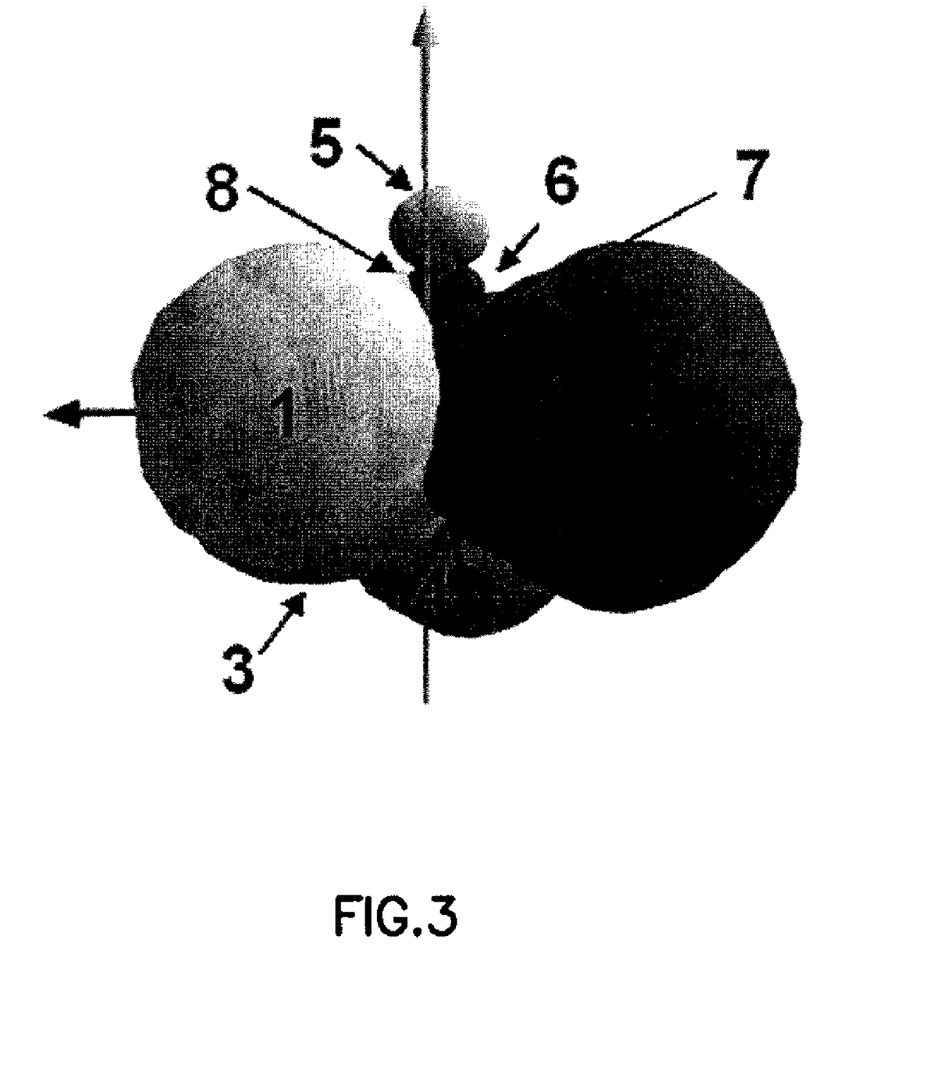
FIG. 3 is a Factor-plot of 240 spectra of different silica phases (1: Nucleosil 1000 (7 µm, 1000 Å); 2: Prontosil 200 (3 µm, 200 Å); 3: Amino A23 (6 µm, 117 Å); 4: Silica 622 (14 µm, 91 Å); 5: Amino 4 (4 µm, 126 Å); 6: Amino A21 (10 µm, 114 Å); 7: ODS 2 (6 µm, 74 ÅA, non endcapped); 8: ODS 3 (6 µm, 78 Å). Conditions: normalization by closure; wave number range: 4500-9996 $cm^{-1}$; reflectance; scans: 10; temperature: 23° C.

FIG. 1 shows electron micrograph pictures of non-porous, 60 Å, 300 Å and 1000 Å particles. Spectra were recorded at 23° C., in the wave number region from 4500 to 9996 cm⁻¹ following the Kubelka-Munk function ($f(R) = (1-R)^2/2R$; $R = I/I_0$). FIG. 2a clearly shows differences in the spectra recorded of the mostly used octadecylated silica (I), amino derivatized silica (II) and pure silica (III). The calculation of their first derivative (Taylor 3 points) allowed to identify and distinguish characteristic absorption bands for each derivatization marked in FIG. 2b. Differences in the HO-saturation degree of the surface are visualized by the differences of their main stretch vibration at 5263 cm⁻¹. The —CH₂ overtone at 5742 cm⁻¹, the —CH₂ and —CH₃ overtone at 5808 cm⁻¹, the 2× C—H str.+C—H def. at 7353 cm⁻¹, the 2× C—H str.+ C—H def. at 7168 cm⁻¹ and the C—H str. 2nd overtone only appear in the spectra of the octadecylated silica. Amino derivatization showed a N—H stretch first overtone at 6538 cm⁻¹. Normalization by closure improved signal to noise ratio and allowed to distinguish between 20 different particles owing different morphology and/or derivatization. A three dimensional display after principal component regression (PCR) and calculation of Mahalanobis-distances in a factor-plot showed that spectra of 8 different silica phases Nucleosil 1000 (7 μm, 1000 Å), Prontosil 200 (3 μm, 200 Å), Amino A23 (6 μm, 117 Å), Silica 622 (14 μm, 91 Å), Amino 4 (4 μm, 126 Å), Amino A21 (10 μm, 114 Å), ODS 2 (6 μm, 74 Å, non endcapped) can be united within one cluster without any outlier spectrum (FIG. 3). On the other hand this offers the possibility to control the rate of synthesis and derivatization during manufacturing. The maximal spectra residual for calibration was 5.47×10⁻⁴ and the resulting Q-value 0.72 (75% of spectra were used for calibration, 25% for validation). To test the suitability of this established system for the discrimination between different particle diameters with the same porosity and surface chemistry, Bischoff Prontosil 3, 5, 10, 15 and 20 μm with a pore diameter of 120 Å was separated in a 3-dimensional factor plot, with a Q-value of 0.95. A Q-value of 0.99 was obtained clustering Bischoff Prontosil with 60, 120, 200 and 300 Å and a constant particle diameter of 5 μm. This demonstrates the sensitivity of the applied method to differences in surface morphology (size, porosity) and/or derivatization.

Quantitative Analysis of Particle Size

Particle size of silica particles is routinely determined by electron microscopy, light scattering or the Coulter-Counter method (Ohmacht, et al. Chromatographia 19, 473 (1984);

Ohmacht et al., Magy Kern 89, 229 (1983)). For the following investigations the particle diameter as provided by the individual producers were taken for calibration. For NIRS determination 230 spectra of 23 different silica and silica based phases were recorded in a wave number range between 4440 and 9000 cm$^{-1}$ in the reflectance mode with the spectrometer. Mathematical pretreatment and statistical analyses were carried out using partial least square regression (PLS). Compared to the Coulter-counter (CC) method, the NIR method allowed the determination of the particle size more precisely with a relative standard deviation in % not higher than 8.6% (Table 1) compared to a variance between +15 and −12% with the Coulter Counter method.

Quantitative Analysis of Specific Surface Area

Figure 5:
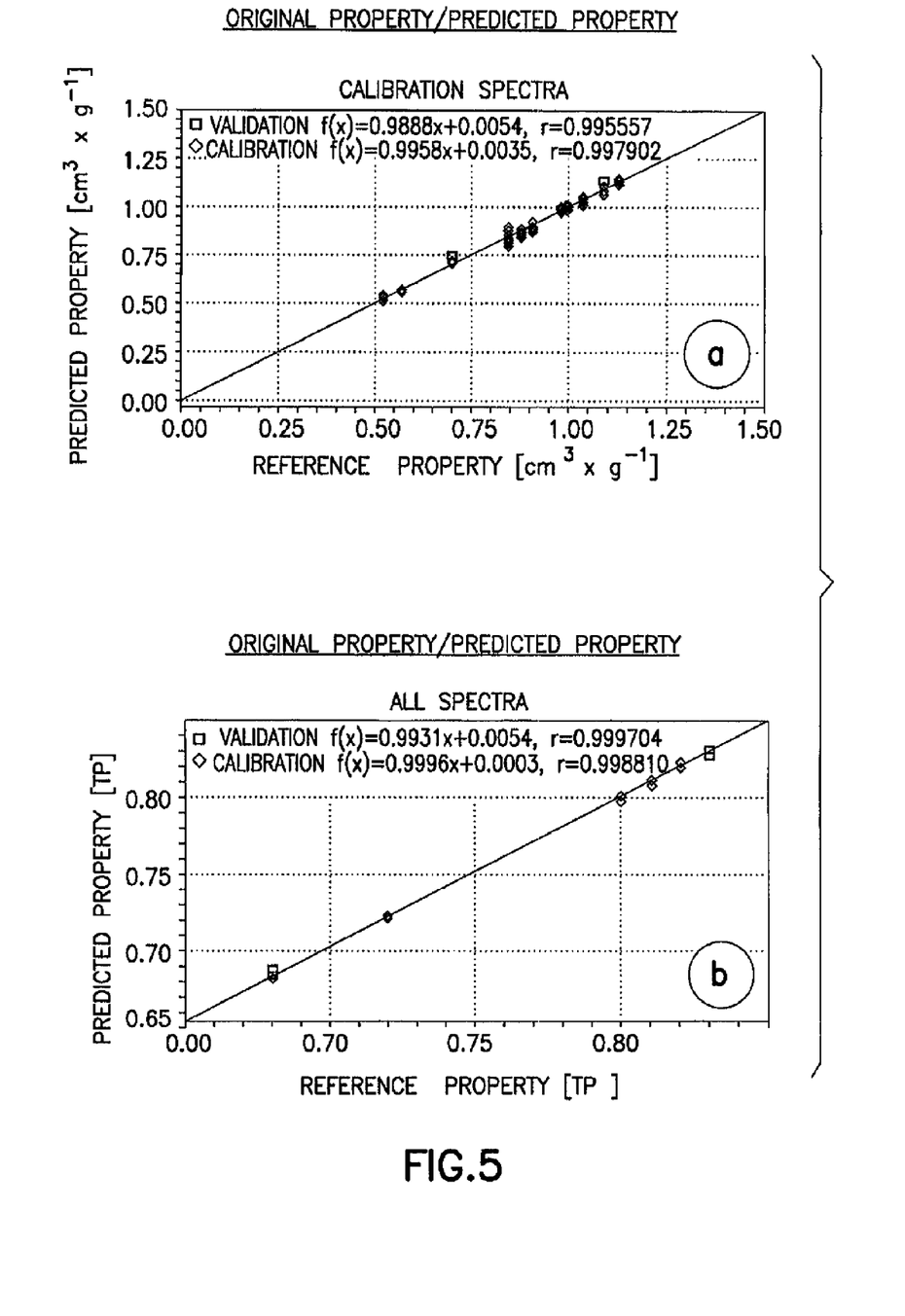
FIG. 5 depicts the predicted (NIRS) versus reference property for the determination of: a: pore volume; b: total porosity. Conditions: a: normalization by closure (4596-9996 $cm^{-1}$), first derivative BCAP, Savitzky Golay 9 points; b: smoothing average 3 points, normalization by closure, first derivative BCAP (4596-9996 $cm^{-1}$); c: normalization by closure, first derivative BCAP, MSC full; scans: 10; reflectance; temperature: 23° C.

Surface areas are usually determined by the BET-method (R. Ohmacht, et al., Chromatographia 19, 473 (1984)), which allows a determination with an RSD % of ±7.8% (Table 1). Recording 230 spectra of 23 silica phases between 4596 and 9996 cm$^{-1}$, calibration using PLS, normalization by closure and calculation of first derivative (BCAP) using 8 primary factors provided values for SEE and SEP of 13.48 and 13.55 m$^2$×g$^{-1}$ and regression coefficients for calibration and validation of >0.99 (FIG. 5b, Table 2). Finally this model allowed the determination of the specific surface area with % RSD <6.8.

TABLE 1

NIR results on physical properties of investigated silica phases:
Particle size, pore diameter, specific surface area (18 selected examples))

| Material | Particle Size [μm] +/−15% RSD[1] Reference | Particle Size [μm] +/−RSD [%] NIR | Pore Diameter [Å] +/−28% RSD[1] Reference | Pore Diameter [Å] +/−RSD [%] NIR | Specific surface area [m$^2$ × g$^{-1}$] +/−7.8% RSD[1] Reference | Specific surface area [m$^2$ × g$^{-1}$] +/−RSD [%] NIR |
|---|---|---|---|---|---|---|
| Amino, 4μ | 4 | 4 +/− 6.5 | 126 | 126 +/− 6.5 | 317 | 317 +/− 4.2 |
| Amino, A21 | 10 | 10 +/− 2.6 | 114 | 114 +/− 7.2 | 317 | 317 +/− 4.2 |
| Amino A 23 | 6 | 6 +/− 4.3 | 117 | 117 +/− 7.0 | 310 | 310 +/− 4.3 |
| Silica 622 | 14 | 14 +/− 1.7 | 91 | 91 +/− 9.0 | 431 | 431 +/− 3.1 |
| Silica 191-1 | 6 | 6 +/− 4.3 | 91 | 91 +/− 9.0 | 458 | 458 +/− 2.9 |
| Silica 191-2 | 6 | 6 +/− 4.3 | 74 | 74 +/− 11.1 | 458 | 458 +/− 2.9 |
| Silica 191-3 | 6 | 6 +/− 4.3 | 74 | 74 +/− 11.1 | 458 | 458 +/− 2.9 |
| ODS 2 (non endc.) | 6 | 6 +/− 4.3 | 74 | 74 +/− 11.1 | 308 | 308 +/− 4.3 |
| ODS 3 (endcap.) | 6 | 6 +/− 4.3 | 78 | 78 +/− 10.9 | 267 | 267 +/− 5.0 |
| Nucleosil 1000 | 7 | 7 +/− 4.3 | 1000 | 1000 +/− 0.8 | 25 | 25 +/− 3.6 |
| S80 Resin | 5.4 | 5.4 +/− 4.8 | 100 | 100 +/− 8.2 | 458 | 458 +/− 2.9 |
| Prontosil 200 | 3 | 3 +/− 8.6 | 200 | 200 +/− 4.1 | 200 | 200 +/− 6.7 |
| Nucleosil 4000 | 7 | 7 +/− 3.7 | 4000 | 4000 +/− 0.2 | 10 | 10 +/− 2.1 |
| Prontosil 120 | 3 | 3 +/− 8.6 | 120 | 120 +/− 6.8 | 300 | 300 +/− 4.5 |
| Prontosil 60 | 3 | 3 +/− 8.6 | 60 | 60 +/− 13.7 | 450 | 450 +/− 0.7 |
| Prontosil 300 | 3 | 3 +/− 8.6 | 300 | 300 +/− 2.7 | 100 | 100 +/− 6.8 |
| Nucleosil C8 | 5 | 5 +/− 5.2 | 120 | 120 +/− 6.8 | 350 | 350 +/− 3.8 |
| Nucleosil C18 | 5 | 5 +/− 5.2 | 300 | 300 +/− 2.7 | 350 | 350 +/− 3.8 |

[1]According method literature reference

Figure 4:
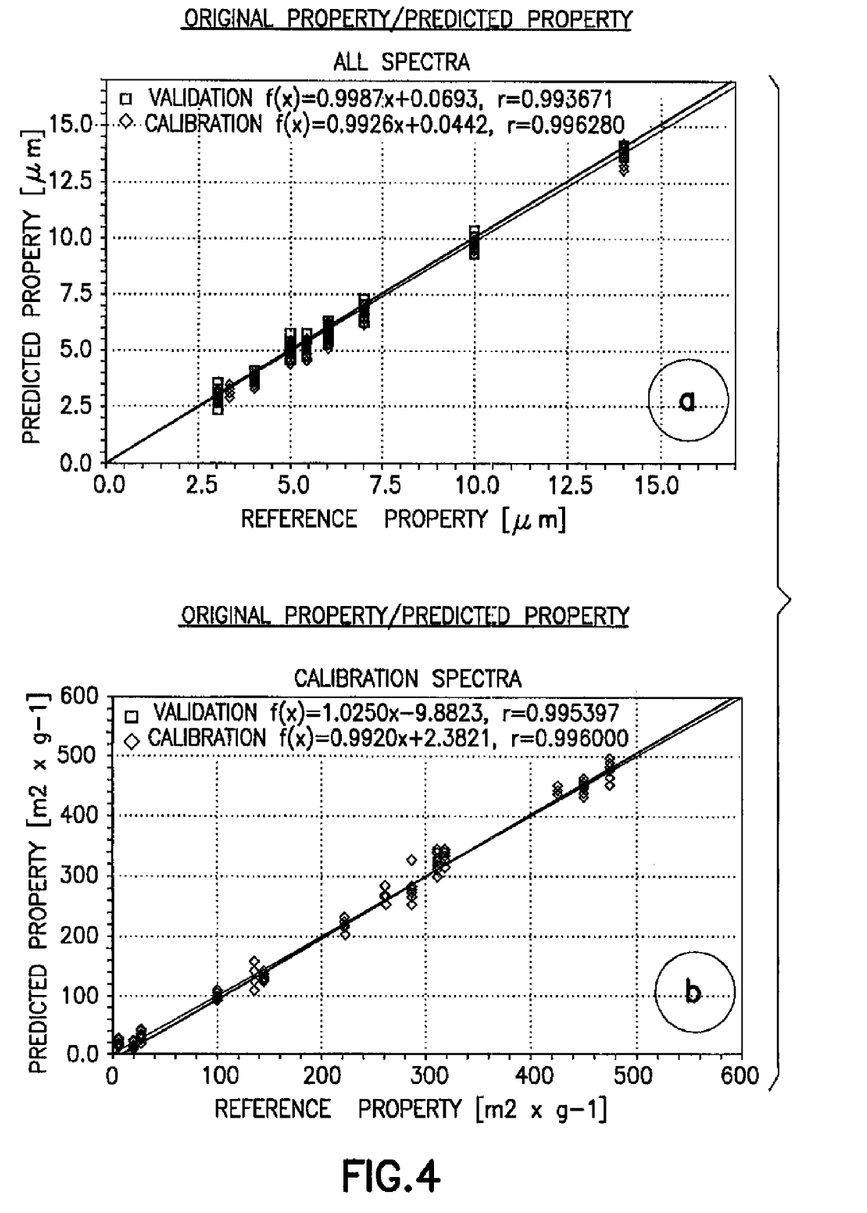
FIG. 4 depicts the predicted (NIRS) versus reference property for the determination of: a: particle diameter; b: specific surface area. Conditions: a: normalization by closure, first derivative BCAP (4440-9000 $cm^{-1}$); b: smoothing average 3 points, normalization by closure, first derivative BCAP (4596-9996 $cm^{-1}$); scans: 10; reflectance; temperature: 23° C.

All recorded spectra were smoothed average 3 points, normalized by closure to improve the signal to noise ratio and finally their first derivative (BCAP) was calculated to minimize shifts in the baseline. 9 primary factors were necessary for the best calibration with values for SEE and SEP of 0.24 and 0.26 μm (Table 2) with regression coefficients for calibration and validation >0.99 (FIG. 4a, Table 2).

Quantitative Analysis of Pore Structure

The description of the pore structure includes determination of pore diameter and volume. Pore diameter and volume are routinely determined by exclusion chromatography (Ohmacht et al., Chromatographia 19, 473 (1984); Ohmacht et al., Chromatographia 14, 155 (1981); Halasz et al,

TABLE 2

Calibration and prediction results for the determination of the particle size,
specific surface area, pore diameter, pore volume, total porosity, pore porosity

| Parameter | Unit | Calibration R$^2$ | Validation r$^2$ | SEE[1] | SEP[2] | BIAS[3] |
|---|---|---|---|---|---|---|
| Particle size | μm | 0.99 | 0.99 | 0.24 | 0.26 | 2.68 × 10$^{-15}$ |
| Specific surface area | m$^2$ × g$^{-1}$ | 0.99 | 0.99 | 13.48 | 13.55 | 1.24 × 10$^{-14}$ |
| Pore diameter | Å | 0.97 | 0.98 | 8.56 | 8.22 | 2.48 × 10$^{-14}$ |
| Pore volume | cm$^3$ × g$^{-1}$ | 0.99 | 0.99 | 0.019 | 0.021 | 1.19 × 10$^{-15}$ |
| Total porosity | n.d. | 0.99 | 0.99 | 9.99 × 10$^{-4}$ | 1.35 × 10$^{-4}$ | 4.41 × 10$^{-15}$ |
| Pore porosity | n.d. | 0.99 | 0.99 | 4.52 × 10$^{-3}$ | 3.05 × 10$^{-3}$ | −3.10 × 10$^{-16}$ |

[1]Standard error of estimation
[2]Standard error of prediction
[3]the average deviation between the predicted values and the actual values of the calibration set Angewandte Chemie 90, 954 (1978); Halasz et al., Berichte der Bunsengesellschaft 79, 731 (1975); Ohmacht, Magy Kern 89, 229 (1983); Werner et al., Chromatogr. Sci. 18, 277 (1980); Crispin et al. Chromatogr. 239, 351 (1981)). The relative standard deviation in percent of pore diameter applying logarithmic Gaussian distribution was found to be between 17 and 28 from the mean value (Table 1). For NIRS investigation 150 spectra of 15 silica particles were recorded from 4596 to 9996 $cm^{-1}$, calibrated by PLS and normalized by closure, calculation of first derivative (BCAP) and smoothing (Savitzky Golay 9 points). 9 primary factors were used for the best calibration model resulting in values for SEE and SEP of 8.56 and 8.22 Å with $R^2$ for calibration and $r^2$ for validation of 0.97 and 0.98 respectively (FIG. 5a, Table 2). The maximum % RSD of the NIR method was 13.7%. Size exclusion chromatography enables the determination of pore volume with 6% RSD. NIRS calibration using PLS, smoothing average 3 points, normalization by closure and first derivative BCAP resulted in a SEE of 0.019 $cm^3 \times g^{-1}$ and a SEP of 0.021 $cm^3 \times g^{-1}$ using 10 primary factors (Table 2). Correlation coefficients for calibration and validation were >0.99 (FIG. 5b), the % RSD <4.03 (Table 1). Furthermore, the NIRS method was also shown to be suitable for the prediction of the total and pore porosity in a packed column assuming a column length of 250 mm and an inner column diameter of 4 mm. The total porosity was determined by SEC following the equation $$\epsilon_T = \epsilon_P + \epsilon_0 = (V_P + V_0)/V_K$$

($V_P$: pore volume [$cm^3$]; $V_0$: intermediate volume [$cm^3$], $V_K$: empty volume [$cm^3$]). A PLS calibration of 150 spectra of 15 samples applying PLS, normalization by closure, first derivative (BCAP) with 14 primary factors allowed the determination with a precision of 0.018% (Table 3) compared to 6% by size-exclusion chromatography (SEC).

The results described point out the general readiness of near infrared reflectance spectroscopy (NIRS) to be used in material science for investigation in the nanometer scale. The generated qualitative model depicted in FIG. 3 also demonstrates clearly the selectivity and even sensitivity of the NIRS method for changes in functionalization. This is shown by the differentiation between the two octadecylated phases ODS2 (6 μm, 74 Å, non endcapped) and ODS 3 (6 μm, 78 Å, endcapped). These materials only differ in the endcapping of free silanol groups. The potential to distinguish between different particle and pore size emphasizes the sensitivity of the method from the micrometer down to the low nanometer region. Nucleosil 1000 (7 μm, 1000 Å) and Prontosil 200 (3 μm, 200 Å) can be differentiated from each other in two unique clusters.

To investigate quantitatively morphological characteristics of the materials individual calibration models for the determination of particle size, surface area and pore structure show a high linearity ($r^2$>0.97). Each calibration model established included silica materials with different functionalities, particle sizes and pore structures in order to make it as robust as possible.

In the following it is proved that these physical parameters can be determined very precisely independent from each other. Particle size can be determined with a linearity >0.99 between 1.5 and 14 μm with RSD less than 8.6% (FIG. 4a).

The quantitative determination of the specific surface area by the NIRS method offers calibration in a wide range between 25 and 458 $m^2 \times g^{-1}$ and allows the determination of the specific surface area with high linearity (r>0.99, FIG. 4b), at a maximum % RSD of 6.7 within a few seconds.

Determination of pore structure via NIRS is easy to carry out and fast. The calibration curve depicted in FIG. 5a shows linearity $r^2$>0.99. It also includes non-porous silica materials,

TABLE 3

NIR results on physical properties of investigated silica phases: Total porosity, pore porosity, pore volume (9 selected examples))

| Material | Total Porosity +/−6% RSD[1] Reference | Total Porosity +/−RSD [%] NIR | Pore Porosity +/−6% RSD[1] Reference | Pore Porosity +/−RSD [%] NIR | Pore volume [$cm^3 \times g^{-1}$] +/−6% RSD[1] Reference | Pore Volume [$cm^3 \times g^{-1}$] +/−RSD [%] NIR |
|---|---|---|---|---|---|---|
| Amino, 4μ | 0.82 | 0.82 +/− 0.016 | 0.41 | 0.41 +/− 0.74 | 1.00 | 1.00 +/− 2.10 |
| Amino, A21 | 0.81 | 0.81 +/− 0.016 | 0.38 | 0.38 +/− 0.80 | 0.90 | 0.90 +/− 2.30 |
| Amino A 23 | 0.80 | 0.80 +/− 0.016 | 0.38 | 0.38 +/− 0.80 | 0.91 | 0.91 +/− 2.30 |
| Silica 622 | 0.83 | 0.83 +/− 0.016 | 0.38 | 0.38 +/− 0.80 | 0.98 | 0.98 +/− 0.10 |
| Silica 191-1 | 0.83 | 0.83 +/− 0.016 | 0.41 | 0.41 +/− 0.74 | 1.04 | 1.01 +/− 4.10 |
| Silica 191-2 | 0.83 | 0.83 +/− 0.016 | 0.41 | 0.41 +/− 0.74 | 1.04 | 1.04 +/− 2.01 |
| Silica 191-3 | 0.83 | 0.72 +/− 0.018 | 0.41 | 0.41 +/− 0.74 | 1.04 | 1.04 +/− 2.01 |
| ODS 2 (non endc.) | 0.72 | 0.72 +/− 0.018 | 0.32 | 0.32 +/− 0.95 | 0.57 | 0.57 +/− 3.68 |
| ODS 3 (endcap.) | 0.68 | 0.68 +/− 0.010 | 0.29 | 0.29 +/− 1.05 | 0.52 | 0.52 +/− 4.03 |

[1] According method literature reference

Values for $r^2$ were >0.99 for calibration and validation equation respectively (Table 2), SEE and SEP were found to be $9.99 \times 10^{-4}$ and $1.35 \times 10^{-4}$ (Table 3). The pore porosity determined by SEC following the equation $\epsilon_P = V_P/V_K$. RSD was found to be in the range of ±6%. Calibration between 4596 and 9996 $cm^{-1}$ by principal component regression (PCR), normalization by closure, calculation of first derivative (Savitzky-Golay 9 points) and normalization to unit length allowed to determine the pore porosity with % RSD <1.05 (Table 3). The values for SEE and SEP were $4.52 \times 10^{-3}$ and $3.05 \times 10^{-3}$ (Table 2), $r^2$ for the calibration and $r^2$ for the validation equations were >0.99 (Table 2).

which fits well into the calibration curve. Total porosity and pore porosity of a packed column are not always determined by SEC, because it is complicated and again time consuming. The high linearity of the predicted total porosity applying the NIRS method can be deduced from FIG. 5b and Table 2. For each individual model the optimum number of factors used for prediction was determined by cross-validation.

These examples clearly demonstrate that NIRS compared to the usual methods has several advantages, such as high linearity, precision, speed, ease of use without sample pretreatment. It can be used for the physicochemical characterization and classification down to the nanoscale.

We claim:

1. A method for characterizing a scientific material selected from the group consisting of silicate material, a polymer material and a nanomaterial, comprising the following steps:
   a) irradiating a measuring light of a predetermined wavelength range into a material specimen,
   b) recording of the measuring light reflected and/or reemitted by the material specimen,
   c) determining a ratio depending on the wave lengths of irradiated to detected measuring light spectrum, and
   d) numerical-mathematical processing spectral data of the material specimen to determine at least one characteristic feature of the material specimen selected from particle size, specific surface area, derivatization, pore porosity, pore size and pore diameter and in the case of polymers the characteristic feature may additionally be one of degree of polymerization, molar mass distribution, crystallinity, thermal phase transitions, branching, stereoregularity and tacticity.

2. A method for characterizing a scientific material selected from the group consisting of silicate material, a polymer material and a nanomaterial, comprising the following steps:
   a) irradiating a measuring light of a predetermined wavelength range into a material specimen,
   b) recording of the measuring light reflected and/or reemitted by the material specimen,
   c) determining a ratio depending on the wave lengths of irradiated to detected measuring light spectrum, and
   d) numerical-mathematical processing of spectral data of each material specimen for determining at least one characteristic feature of the material specimen,
   wherein the silicate material is a silica gel, the polymer material is a poly(styrene/divinylbenzene) (PS/DVB) or a poly(glycidylmethacrylate/divinylbenzene) and the nanomaterial is a derivatized nanomaterial.

3. The method according to claim 2, wherein the characteristic features of the material specimen determined by numerical-mathematical processing are particle size, specific surface area, derivatization, pore porosity, pore size and/or pore diameter and in the case of polymers the characteristic feature may additionally be one of degree of polymerization, molar mass distribution, crystallinity, thermal phase transitions, branching, stereoregularity and tacticity.

4. A method for characterizing a scientific material selected from the group consisting of silicate material, a polymer material and a nanomaterial, comprising the following steps:
   a) irradiating a measuring light of a predetermined wavelength range into a material specimen,
   b) recording of the measuring light reflected and/or reemitted by the material specimen,
   c) determining a ratio depending on the wave lengths of irradiated to detected measuring light spectrum, and
   d) numerical-mathematical processing of spectral data of each material specimen for determining at least one characteristic feature of the material specimen,
   wherein the predetermined wavelength range is in the wavelength range of approximately 1,000 to 2,500 nm (4,500-14,186 cm$^{-1}$).

5. The method according to claim 1, wherein the measuring light is conducted to the material specimens via a light conductor and/or is absorbed by the material specimens.

6. The method according to claim 1, wherein a layer of the material specimens has an optical thickness in the range of approximately 0.2 to 5 mm.

7. The method according to claim 1, wherein the material specimens are thermostated to a maintain a constant temperature for the measurement.

8. A method for characterizing a scientific material selected from the group consisting of silicate material, a polymer material and a nanomaterial, comprising the following steps:
   a) irradiating a measuring light of a predetermined wavelength range into a material specimen,
   b) recording of the measuring light reflected and/or reemitted by the material specimen,
   c) determining a ratio depending on the wave lengths of irradiated to detected measuring light spectrum, and
   d) numerical-mathematical processing of spectral data of each material specimen for determining at least one characteristic feature of the material specimen,
   wherein the numerical-mathematical processing comprises a data reduction, by at least one of: normalization, smoothing, $1^{st}$ derivation, $2^{nd}$ derivation, multiplicative scatter correction, reciprocal value, square, mean centering, Kubelka Munc Transformation, absorption, baseline correction, addition of a constant, shift negative to zero, principal component analysis (PCA), principal component regression (PCR), and partial least squares regression (PLS).

9. A method for characterizing a scientific silicate material, a polymer material or a nanomaterial comprising the following steps:
   a) providing a plurality of material classes each with a plurality of calibration and material specimens per class with a plurality of known class-characteristics;
   b) irradiating a measuring light of a predetermined wavelength range into the material specimen;
   c) recording of the measuring light passed through, reflected, reemitted and/or scattered by the material specimens;
   d) determining a ratio depending on the wave lengths of irradiated to detected measuring light (spectrum) for each material specimen of a class;
   e) numerical-mathematical processing of spectral data of each material specimen;
   f) correlating the spectra of a majority of material specimens with a predetermined material class;
   g) creating a database with the processed spectral data with different material classes based on the material specimens measured of individual classes for calibration of a class correlation;
   h) repeating steps b) to e) at least once with at least one material sample with at least partially unknown characteristics; and
   i) determining the material classes to which the unknown material specimen is related, by means of a class correlation of the spectra measured using the created calibration database from step g).

10. The method according to claim 9, wherein the silicate material is a silica gel, the polymer material is a poly(styrene/divinylbenzene)(PS/DVB) or a poly(glycidyl-methacrylate/divinylbenzene) and the nanomaterial is a derivatized nanomaterial.

11. The method according to claim 9, wherein the characteristics of the individual material classes determined by numerical-mathematical processing is at least one of: particle size, particle surface, pore diameter, pore volume, derivatization and pore porosity and in the case of polymers the characteristic feature may additionally be one of degree of polymerization, molar mass distribution, crystallinity, thermal phase transitions, branching, stereoregularity and tacticity.

12. The method according to claim 9, wherein the wavelength is in the wavelength range of approximately 1,000 to 2,500 nm (4,500-14,286 cm$^{-1}$).

13. The method according to claim 9, wherein the measuring light is conducted via a light conductor to the material specimens and/or is absorbed by same.

14. The method according to claim 9, wherein a layer of the material specimens has an optical thickness in the range of approximately 0.2 to 5 mm.

15. The method according to claim 9, wherein the material specimens are thermostated to maintain a constant temperature for the measurement.

16. The method according to claim 9, wherein the numerical-mathematical processing comprises a data reduction selected from: normalization, smoothing, 1st derivation, 2nd derivation, multiplicative scatter correction, reciprocal value, square, mean centering, Kubelka Munc Transformation, absorption, baseline correction, addition of a constant, shift negative to zero, principal component analysis (PCA), principal component regression (PCR), and partial least squares regression (PLS).

17. The method according to claim 9, wherein the correlation of the numerically-mathematically processed spectral data is by at least one multivariate method selected from principal component analysis (PCA) and/or a smoothing, and/or at least one series expansion and/or artificial neuronal network algorithm, Dynamic Learning Vector Quantization (DLVQ-algorithm), Radial Basis Functions (RBF-networks).

18. The method according to claim 9, wherein the correlation is caused by formation of clusters.

19. The method according to claim 18, wherein tolerance areas of individual clusters are adjustable during calibration.

20. The method according to claim 9, wherein approximately 3 to 20 spectral-scans/material specimen are recorded.

21. The method according to claim 9, wherein approximately 10 material specimen per class characteristic are recorded for calibration.

22. The method according to claim 9, wherein approximately 70% of all material specimens measured per class are used for calibration and approximately 30% are used for validating the procedure.

23. The method according to claim 9, wherein classification results are shown as 3D-plot.

* * * * *